United States Patent
Ishikawa et al.

(10) Patent No.: US 9,603,940 B2
(45) Date of Patent: *Mar. 28, 2017

(54) METAL SALEN COMPLEX DERIVATIVE AND PROCESS FOR PRODUCTION THEREOF

(75) Inventors: Yoshihiro Ishikawa, Tokyo (JP);
Haruki Eguchi, Kawasaki (JP);
Hiroshi Sato, Yokohama (JP)

(73) Assignees: IHI Corporation, Tokyo (JP);
Yoshihiro Ishikawa, Tokyo (JP)

( * ) Notice: Subject to any disclaimer, the term of this patent is extended or adjusted under 35 U.S.C. 154(b) by 435 days.

This patent is subject to a terminal disclaimer.

(21) Appl. No.: 13/639,656

(22) PCT Filed: Apr. 6, 2011

(86) PCT No.: PCT/JP2011/002056
§ 371 (c)(1),
(2), (4) Date: Oct. 5, 2012

(87) PCT Pub. No.: WO2011/125331
PCT Pub. Date: Oct. 13, 2011

(65) Prior Publication Data
US 2013/0029399 A1  Jan. 31, 2013

(30) Foreign Application Priority Data

Apr. 6, 2010  (JP) .................. 2010-088113

(51) Int. Cl.
| | | |
|---|---|---|
| *A61K 51/00* | (2006.01) | |
| *A61M 36/14* | (2006.01) | |
| *A61K 47/48* | (2006.01) | |
| *A61K 9/00* | (2006.01) | |
| *A61K 41/00* | (2006.01) | |

(52) U.S. Cl.
CPC ...... *A61K 47/48076* (2013.01); *A61K 9/0009* (2013.01); *A61K 41/00* (2013.01)

(58) Field of Classification Search
CPC ........ A61K 9/00; A61K 9/0009; A61K 41/00; A61K 47/00; A61K 47/48076; A61K 2121/00; A61K 2123/00
USPC ... 424/1.11, 1.49, 1.53, 1.65, 1.73; 435/188; 530/300, 391.1, 400; 536/23.1
See application file for complete search history.

(56) References Cited

U.S. PATENT DOCUMENTS

| | | | |
|---|---|---|---|
| 5,880,149 A * | 3/1999 | Grinstaff et al. ............. | 514/492 |
| 6,184,322 B1 | 2/2001 | Styring | |
| 7,371,579 B1 * | 5/2008 | Rokita et al. ................. | 436/86 |
| 2003/0044408 A1 | 3/2003 | Levy | |
| 2005/0224761 A1 | 10/2005 | Von Kiedrowski | |
| 2009/0169484 A1 * | 7/2009 | Eguchi ............... | A61K 41/0052 424/9.36 |

| | | |
|---|---|---|
| 2009/0253149 A1 | 10/2009 | Ahrens |
| 2009/0286968 A1 | 11/2009 | Gorden |
| 2009/0326061 A1 | 12/2009 | Mandal |

FOREIGN PATENT DOCUMENTS

| | | |
|---|---|---|
| JP | 2009-173631 | 8/2009 |
| JP | 2009-196913 | 9/2009 |
| JP | 2009-196914 | 9/2009 |
| JP | 2009-256232 | 11/2009 |
| JP | 2009-256233 | 11/2009 |
| JP | 2009-274962 | 11/2009 |
| JP | 2009-287949 | 12/2009 |
| WO | 9749671 A1 | 12/1997 |
| WO | 0102370 A1 | 1/2001 |
| WO | 02103004 A1 | 12/2002 |
| WO | 03095478 A1 | 11/2003 |
| WO | 2005011738 A2 | 2/2005 |
| WO | 2009052436 A1 | 4/2009 |

OTHER PUBLICATIONS

Barath et al, Chem. Commun., 2010, vol. 46, pp. 7391-7393.*
Laskin et al , J. Am. Chem. Soc., 2008, vol. 130, pp. 3218-3230.*
International Search Report from International Application No. PCT/JP2011/002056 mailed Jun. 14, 2011.
Reetz Manfred T., et al. "Directed evolution of enantioselective hybrid catalysts: a novel concept in asymmetric catalysis".
Routier Sylvain, et al. "Synthesis, DNA Binding and Cleaving Properties of an Ellipticine—Salen. Copper Conjugate".
Shen et al, Principle of Polymer Materials Processing (second Edition), Beijing, China, Textile & Apparel Press, Mar. 2009.
Chinese Office Action dated Feb. 15, 2015.
V. Nadeau et al, "Synthesis and Characterization of biodegradable and charged salen-based polymers", Journal of Applied Polymer Science, vol. 102, No. 3, Nov. 5, 2006, pp. 2568-2577.
V. Nadeau et al, "Afm study of a new carrier based on PLA and salen copolymers for gene therapy", Molecules (Basel Switzerland), 2005, vol. 10, No. 1, pp. 105-113.
V. Madhavan et al, "Macrocyclic Cyclooctene-Supported AICl-Salen Catalysts for Conjugated Addition Reactions: Effect of Linker and Support Structure on Catalysis", Chemistry-A European Journal, vol. 15, No. 5, Jan. 19, 2009, pp. 1186-1194.
M. Nielsen et al "DNA-Directed Coupling of Organic Modules by Multiple Parallel Reductive Aminations and Subsequent Cleavage of Selected DNA Sequences", Bioconjugate Chemistry, vol. 16, No. 4, Jul. 1, 2005, pp. 381-985.

(Continued)

*Primary Examiner* — D L Jones
(74) *Attorney, Agent, or Firm* — Brundidge & Stanger, P.C.

(57) ABSTRACT

A metal-salen complex derivative with an excellent yield and stability is provided and a method for producing such a metal-salen complex derivative is provided. The present invention provides: metal-salen complex derivative obtained by allowing a target component composed of at least one of an enzyme, an antibody, an antigen, a peptide, an amino acid, an oligonucleotide, a protein, a nucleic acid, and a medical molecule to bind to a metal-salen complex via an amide bond or a disulfide bond; a method for producing such a metal-salen complex derivative.

2 Claims, No Drawings

(56) References Cited

OTHER PUBLICATIONS

Routier S, et al, "Salen-anthraquinone conjugates: Synthesis, DNA-binding and cleaving properties, effects on topoisomerases and cytotoxicity", American Association for Cancer Research, Proceedings of the Annual Meeting, American Association for Cancer Research, US, vol. 37, Mar. 1996, p. 435, including an English Abstract dated August 1996.
EESR Report dated Feb. 5, 2016.

* cited by examiner

METAL SALEN COMPLEX DERIVATIVE AND PROCESS FOR PRODUCTION THEREOF

TECHNICAL FIELD

The present invention relates to a metal-salen complex derivative and a method for producing the metal-salen complex derivative.

BACKGROUND ART

An iron-salen complex that is known as a metal catalyst is known as a metal-salen complex. Also, the applicant has clarified that the iron-salen complex itself has magnetic properties and further has antitumor effects; and the applicant suggests that the iron-salen complex can be guided to a target affected site and the pharmacological effects of the iron-salen complex can be concentrated locally by administering the iron-salen complex to a human or an animal and then applying a magnetic field to the human/animal body externally.

Moreover, the applicant has clarified that a medical molecule can be guided to the affected site tissue by means of a magnetic field by allowing the iron-salen complex to bind to the medical molecule. This iron-salen complex is disclosed in Japanese Patent Application Laid-Open (Kokai) Publication No. 2009-173631, Japanese Patent Application Laid-Open (Kokai) Publication No. 2009-196913, Japanese Patent Application Laid-Open (Kokai) Publication No. 2009-196914, Japanese Patent Application Laid-Open (Kokai) Publication No. 2009-256232, Japanese Patent Application Laid-Open (Kokai) Publication No. 2009-256233, and Japanese Patent Application Laid-Open (Kokai) Publication No. 2009-274962.

Furthermore, in Japanese Patent Application Laid-Open (Kokai) Publication No. 2009-287949, the applicant suggests an antibody or antigen determination method capable of separating a bound antigen or antibody from a free antigen or antibody by means of magnetism by connecting the antibody and antigen to the iron-salen complex by means of a biotin-avidin reaction.

CITATION LIST

Patent Literature

[Patent Literature 1] Japanese Patent Application Laid-Open (Kokai) Publication No. 2009-173631
[Patent Literature 2] Japanese Patent Application Laid-Open (Kokai) Publication No. 2009-196913
[Patent Literature 3] Japanese Patent Application Laid-Open (Kokai) Publication No. 2009-196914
[Patent Literature 4] Japanese Patent Application Laid-Open (Kokai) Publication No. 2009-256232
[Patent Literature 5] Japanese Patent Application Laid-Open (Kokai) Publication No. 2009-256233
[Patent Literature 6] Japanese Patent Application Laid-Open (Kokai) Publication No. 2009-274962
[Patent Literature 7] Japanese Patent Application Laid-Open (Kokai) Publication No. 2009-287949

SUMMARY OF INVENTION

However, the above-described conventional technology cannot allow sufficient bonding between the metal-salen complex and, for example, the medical molecule, the antigen, and the antibody and has the problem of the yield and stability of the metal-salen complex derivative. So, it is an object of the present invention to provide a metal-salen complex derivative with an excellent yield and stability and a method for producing such a metal-salen complex derivative.

In order to achieve the above-described object, the present invention is characterized that it is: a metal-salen complex derivative obtained by allowing a functional molecule composed of at least one of an enzyme, an antibody, an antigen, a peptide, an amino acid, an oligonucleotide, a protein, a nucleic acid, and a medical molecule to bind to a metal-salen complex via at least one of a disulfide bond, an ether bond, an ester bond, and an amide bond; and a method for producing such a metal-salen complex derivative. Bonding between the metal-salen complex and the functional molecule is preferably formed via a crosslinker for forming a crosslink between them.

Specifically speaking, the present invention is characterized is that it is a metal-salen complex derivative represented by A-B-C (A: a metal-salen complex; B: a bond area including at least one of a disulfide bond, an ether bond, an ester bond, and an amide bond; C: a functional molecule composed of at least one of an enzyme, an antibody, an antigen, a peptide, an amino acid, an oligonucleotide, a protein, a nucleic acid, and a medical molecule).

A preferred embodiment of the present invention is that the bond area (B) includes a crosslinker molecule for forming a crosslink between the metal-salen complex (A) and the functional molecule (C), the metal-salen complex (A) and the crosslinker molecule are bound together via the disulfide bond, ether bond, ester bond, or amide bond, the crosslinker molecule and the functional molecule (C) are bound together via the disulfide bond, ether bond, ester bond, or amide bond.

The metal-salen complex (A) is not particularly limited and, for example, is represented by the following formula (I).

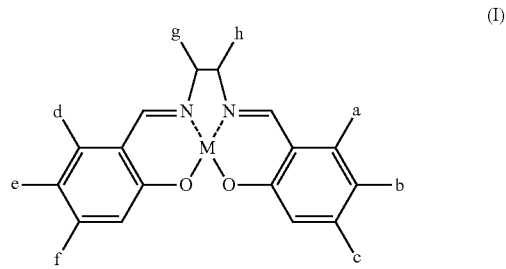

(I)

At least one of a to h is the "—B—C" and the rest is a hydrogen or an arbitrary substituent. The substituent may be anything that can form the bond area with the crosslinker molecule and/or the functional molecule and may be, for example, at least one of a hydroxyl group, an amide group, a carboxyl group, and an SH group. Incidentally, a monomer as shown in (I) or a polymer including a dimer, in which a metal atom portion is mutually bound with each other directly or via another atom (such as an enzyme).

M is a metal atom such as Fe, Cr, Mn, Co, Ni, Mo, Ru, Rh, Pd, W, Re, Os, Ir, Pt, Nd, Sm, Eu, or Gd.

The disulfide bond area (B) is obtained as a result of bonding between an SH group introduced as a substituent to the metal-salen complex (A) and an SH group of the functional molecule (C) or is obtained as a result of bonding between an SH group of the metal-salen complex (A) or the functional molecule (C) and an SH group of the crosslinker molecule.

The ether bond area (B) is obtained as a result of bonding between a hydroxyl group introduced as the substituent to the metal-salen complex (A) and a hydroxyl group of the functional molecule (C) or is obtained as a result of bonding between a hydroxyl group of the metal-salen complex (A) or the functional molecule (C) and a hydroxyl group of the crosslinker molecule.

The ester bond area (B) is obtained as a result of bonding between a hydroxyl group or carboxyl group introduced as the substitutent to the metal-salen complex (A) and a carboxyl group and hydroxyl group of the functional molecule (C) or is obtained as a result of bonding between a hydroxyl group or carboxyl group of the metal-salen complex (A) or the functional molecule (C) and a carboxyl group or hydroxyl group of the functional molecule (C).

The amide bond area (B) is obtained as a result of bonding between an amide group or carboxyl group introduced as the substitutent to the metal-salen complex (A) and a carboxyl group or amide group of the functional molecule (C) or is obtained as a result of bonding between a carboxyl group or amide group of the metal-salen complex (A) or the functional molecule (C) and an amide group and carboxyl group of the functional molecule (C).

Advantageous Effects of Invention

A metal-salen complex derivative which has a good yield and stability and is composed of a combination of a functional molecule, such as a medical molecule, and a metal-salen complex can be provided according to the present invention as described above.

EMBODIMENTS FOR CARRYING OUT THE INVENTION

The disulfide bond area (B) includes, for example, a crosslinker molecule having the following formula (II).

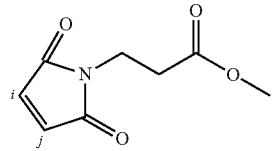

(II)

The metal-salen complex (A) binds to ".O—" in (II) and a disulfide group (—S—S—) which binds to the functional molecule (C) binds to at least one of i and j.

Another example of the crosslinker in the disulfide bond area (B) has the following structure (III).

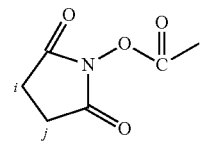

(III)

The metal-salen complex (A) binds to ".C(O)—" in (III) and the disulfide group which binds to the functional molecule (C) binds to at least one of i and j.

Another crosslinker in the disulfide bond area (B) has the following structure

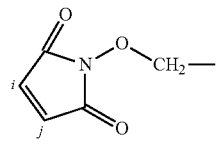

(IV)

The metal-salen complex (A) binds to ".CH$_2$—" in (IV) and the disulfide group which binds to the functional molecule (C) binds to at least one of i and j.

In a preferred embodiment where the functional molecule (C) such as an enzyme is directly bound with the metal-salen complex, the metal-salen complex and a condensation assistant molecule may be dehydrated and condensed to generate their active ester (intermediate) and the amino group of the functional molecule (3) may be made to react to the active ester, thereby substituting the condensation assistant molecule of the active ester, forming an amide bond, and binding the metal-salen complex with the target component via the amide bond. This is shown in the following reaction formula.

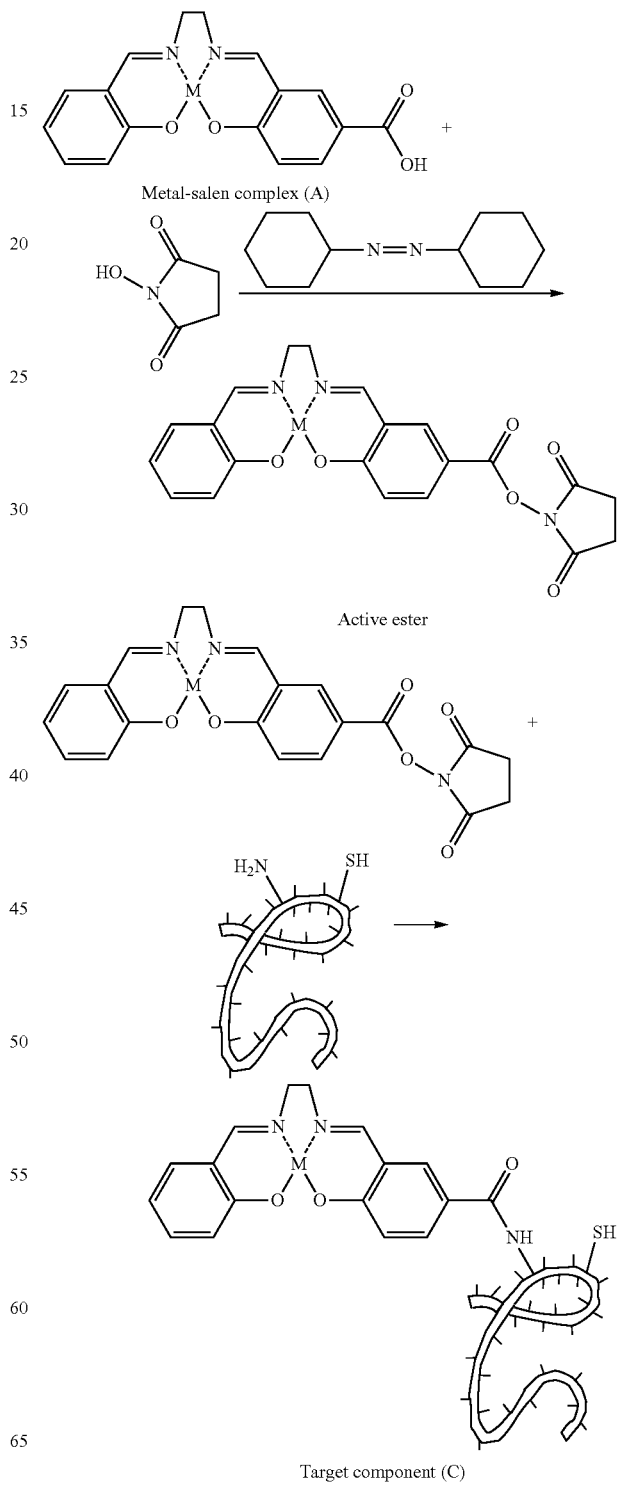

Under the above-described circumstance, N,N'-dicyclohexyl carbodiimide (DCC) is a dehydration condensation agent molecule and N-hydroxysuccinimide (H ONSu) is a condensation assistant molecule.

The aforementioned condensation assistant molecule (H ONSu) can be used as the crosslinker molecule to bind the metal-salen complex (A) with the functional molecule (C). The metal-salen complex and the condensation assistant molecule are condensed and an SH group of the condensation assistant molecule and an SH group of the functional molecule are made to react to each other, thereby forming a disulfide bond and binding the metal-salen complex and the functional molecule together via the disulfide bond.

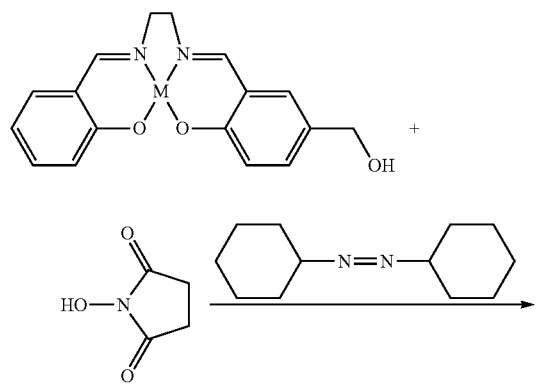

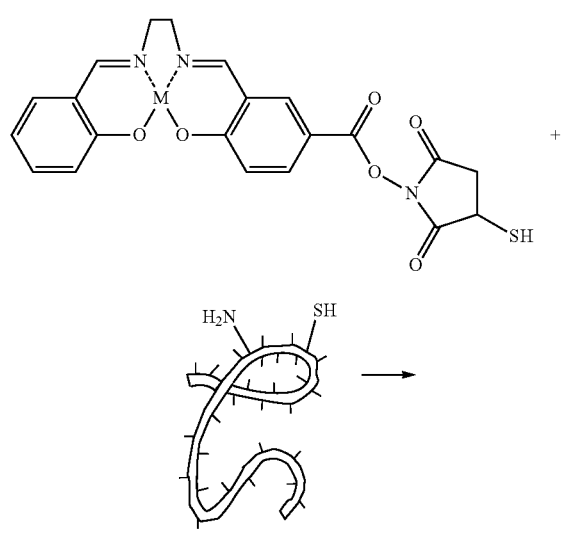

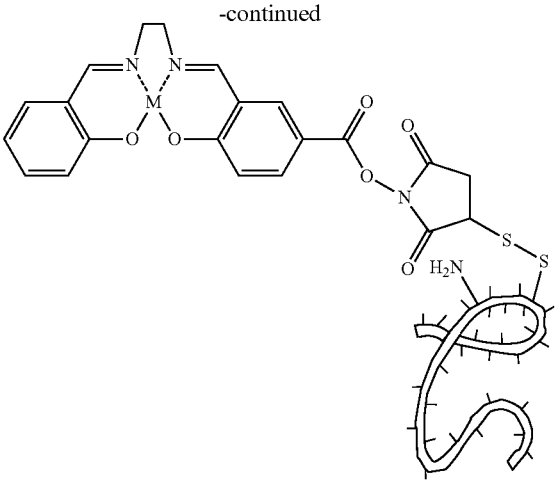

The metal-salen complex has a functional group for condensation with a functional group of the crosslinker molecule, in at least one of the aforementioned a-h side chains so that it can be condensed with the crosslinker molecule. For example, the metal-salen complex has a functional group (carboxyl group or hydroxyl group) for dehydration and condensation with a hydroxyl group of the cross linker molecule, in at least one of the aforementioned a-h side chains so that the metal-salen complex can be condensed with the crosslinker molecule (condensation assistant molecule: H ONSu)).

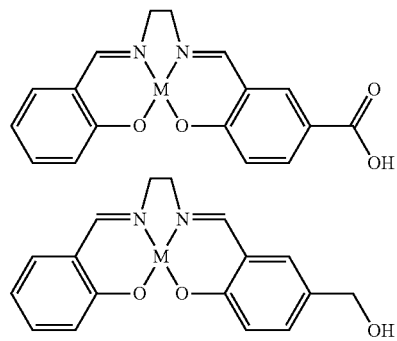

Examples of the crosslinker molecule (condensation assistant molecule) include the following:
Carbodiimide Condensation Agent:
diisopropyl carbodiimide (DIPC);
1-ethyl-3-(3-dimethylaminopropyl)-carbodiimide (EDC=WSCI);
1-ethyl-3-(3-dimethylaminopropyl)-carbodiimide hydrochloride (WSCI.HCl); and
dicyclohexyl carbodiimide (DCC).
Fluorophosphate Condensation Agent:
O-(7-azabenzotriazole-1-yl)-1,1,3,3-tetramethyluronium hexafluorophosphate;
O-benzotriazole-1-yl-N,N,N',N'-tetramethyluronium hexafluorophosphate;
benzotriazole-1-yl-oxy-tris-pyrrolidinophosphonium hexafluorophosphate; and
benzotriazole-1-yl-tris(dimethylamino)phosphonium hexafluorophosphate (BOP).
Others:
diphenyl phosphoryl azide (DPPA).
Examples of the aforementioned condensation assistant include the following.

N-hydroxy polyvalent caroboxylic acid imides:
N-hydroxysuccinimide (HONSu); and
N-hydroxy-5-norbornene-2,3-dicarboxylic acid imide (HONB).
N-hydroxy triazoles:
1-hydroxybenzotriazole (HOBt).
Others:
3-hydroxy-4-oxo-3,4-dihydro-1,2,3-benzotriazine (HOObt);
2-hydroxyimino-2-ethyl cyanoacetate ester;
p-nitrophenol (HONp); and
pentafluorophenol (HOPfp).

Distribution of the metal-salen complex, the condensation assistant, and the condensation agent is, for example, as follows:
metal-salen complex:condensation assistant:condensation agent=1:1 to 2:1 to 2.

Bonding between the target component and the metal-salen complex can be confirmed by mass spectrometry. Generation of the amide bond and the disulfide bond can be confirmed by mass spectrometry and IR spectroscopy.

Examples

Metal-Salen Complex Production Examples

Next, a metal-salen complex including an amino group as a substituent was produced as explained below.

Step 1:

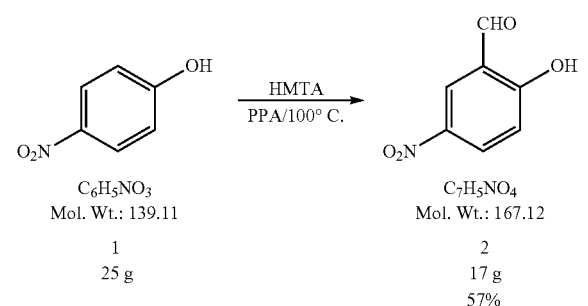

A mixture of 4-nitrophenol (25 g, 0.18 mol), hexamethylene tetramine (25 g, 0.18 mol), and polyphosphoric acid (200 ml) was stirred for 1 hour at 100° C. The mixture was then introduced into 500 ml of ethyl acetate and 1 L of water, and was stirred until completely dissolved. When 400 ml of ethyl acetate was further added to the solution, the solution separated into two phases, the aqueous phase was removed, and the remaining compound was washed twice with a basic solvent and dried over anhydrous MgSO4, allowing 17 g of Compound 2 to be synthesized (57% yield).

Step 2:

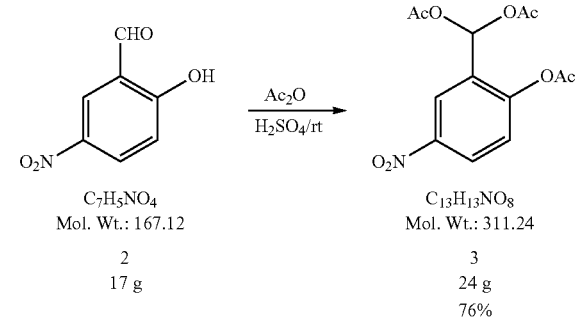 [SMILES: "Ac2O" ; O=Cc1cc([N+](=O)[O-])ccc1O ; CC(=O)Oc1ccc([N+](=O)[O-])cc1C(OC(C)=O)OC(C)=O]

Compound 2 (17 g, 0.10 mol), acetic anhydride (200 ml), and sulfunic acid (minimal: approximately 15 ml) were stirred for 1 hour at room temperature. The resulting solution was mixed for 0.5 hour in iced water (2 L) to bring about hydrolysis. The resulting solution was filtered and dried in the atmosphere, giving white powder. The powder was recrystallized from a solution containing ethyl acetate, giving 24 g of Compound 3 (76% yield) in the form of white crystals.

Step 3:

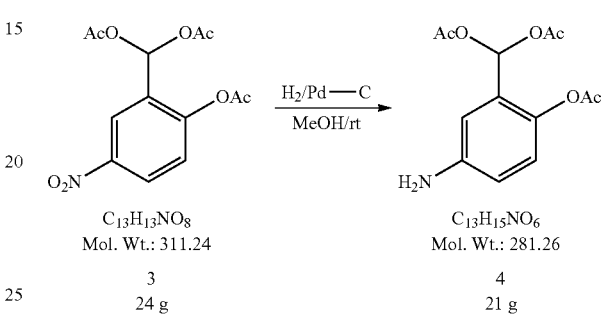

A mixture of carbon (2.4 g) carrying 10% palladium with Compound 3 (24 g, 77 mmol) and methanol (500 ml) was reduced over night in a 1.5 atm hydrogen reducing atmosphere. After the reduction was completed, the product was filtered, thereby allowing Compound 4 (21 g) in the form of brown oil to be synthesized.

Step 4, 5:

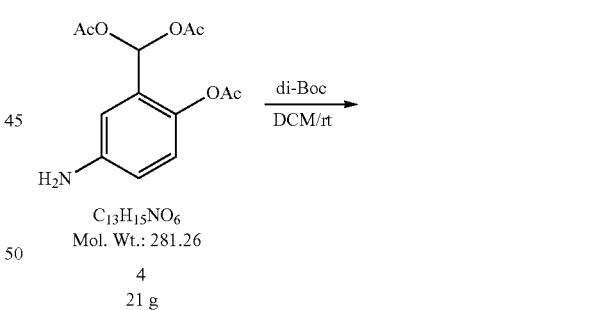

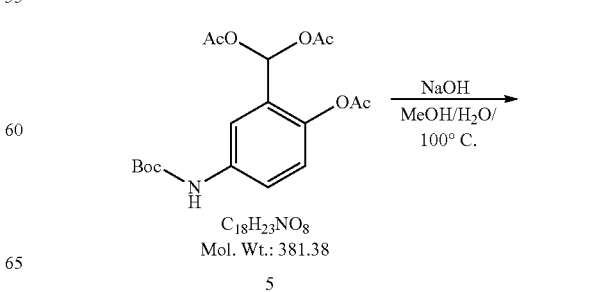

-continued

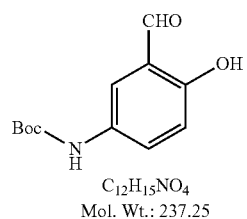

C₁₂H₁₅NO₄
Mol. Wt.: 237.25

6
10 g
58%

Compound 4 (21 g, 75 mmol) and di(tert-butyl)dicarbonate (18 g, 82 mmol) were stirred over night in anhydrous dichloromethane (DCM) (200 ml) in a nitrogen atmosphere. The resulting solution was allowed to evaporate in a vacuum and then dissolved in methanol (100 ml). Sodium hydroxide (15 g, 374 mmol) and water (50 ml) were then added, and the solution was brought to reflux for 5 hours. The solution was then cooled, filtered, washed with water, and allowed to dry in a vacuum, thereby giving a brown compound. The resulting compound was processed twice by flash chromatography using silica gel, thereby giving 10 g of Compound 6 (58% yield).

Step 6:

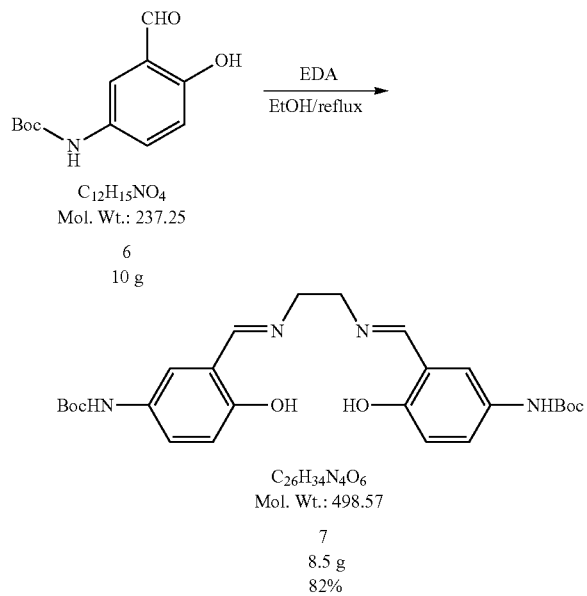

C₁₂H₁₅NO₄
Mol. Wt.: 237.25

6
10 g

C₂₆H₃₄N₄O₆
Mol. Wt.: 498.57

7
8.5 g
82%

Compound 6 (10 g, 42 mmol) was introduced into 400 ml of anhydrous ethanol, the mixture was brought to reflux while heated, and several drops of ethylene diamine (1.3 g, 21 mmol) were added while stirred for 0.5 hour into 20 ml anhydrous ethanol. The mixture solution was introduced into a container of ice, where it was cooled and mixed for 15 minutes. It was then washed with 200 ml ethanol, filtered, and dried in a vacuum, thereby giving 8.5 g (82% yield) of Compound 7.

Examples of Bonding Between Iron-Salen Complex and Protein (Disulfide Bond)

Step 1:

Compound 7A

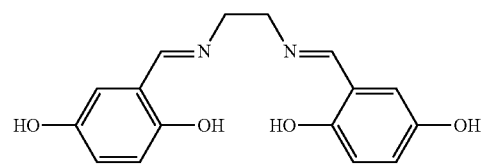

Compound 8

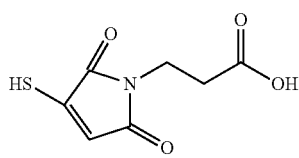

Compound 8 was prepared by referring to Manfred T. Reetz, Martin Rentzsch, Andreas Pletsch, Matthias Maywald, Peter Maiwald, Jerome j.-P. Peyralans, Andrea Maichele, Yu Fu, Ning Jiao, Frank Hollmann, Regis Mondiere and Andreas Taglieber, 'Direct evolution of enantioselective hybrid catalysis: a novel concept in asymmetric catalysis,' Tetrahedron 63 (2007) 6404-6414.

Step 2:

Compound 7A (134 mg, 0.338 mmol), Compound 8 (122 mg, 0.721 mmol), the crosslinker molecule, diisopropylcarbodiimide (170 μmol), the dehydration condensation agent, and NaHCO₃ (75 mg; 0.89 mmol) were put in a solution in which 0.1 M of N,N-4-dimethylaminopyridin was dissolved in THF (tetrahydrofuran) (20 ml), and the resulting solution was stirred for 2 hours at room temperature. The solution was mixed with a solution, in which ethyl acetate and hexane were mixed in a 1:1 ratio, and the solution was processed by chromatograpy using silica gel (20 g), thereby getting Compound 9 (yellow, 115 g, 62% yield).

Compound 9

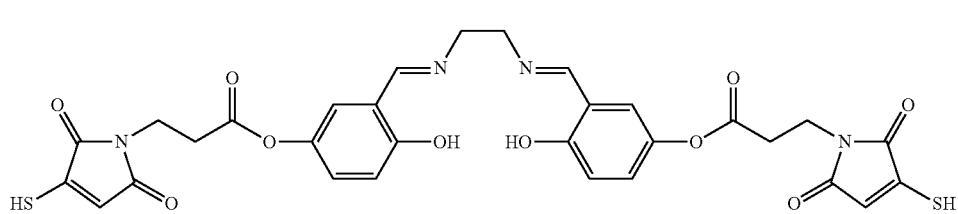

Step 3:

Compound 9 (17 mg, 31 μmol) and FeCl₃ (11 mg) were put in methanol (4 ml) and stirred for 16 hours in the atmosphere at room temperature, thereby obtaining a brown compound. The compound was then dried in a vacuum. The resulting compound was diluted with 400 ml of dichloromethane, washed twice with a saline solution, dried over anhydrous Na₂SO₄, and dried in a vacuum, thereby obtaining Compound 10 (18 mg, 90% yield).

Compound 10

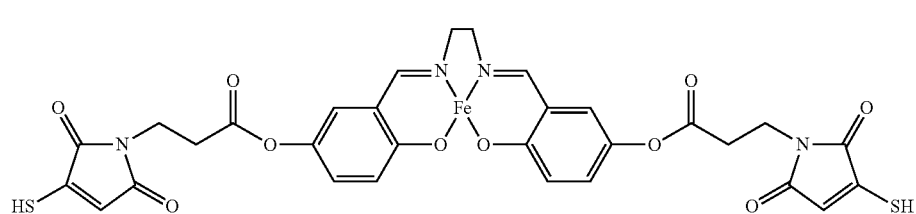

Step 4:

Compound 10, protein purchased from Sigma-Aldrich (papain-lyophilisate, 10 mg), and L-cysteine (10 mg) were put in water (H₂O, 1 ml) and stirred for 30 minutes. Then, the resulting solution was stirred with a phosphate buffer (300 μl, 1 M) at pH=7.01. Six hours after stirring, Compound 11 and Compound 12 were synthesized (Papain binds to SH groups in both of them).

Compound 11

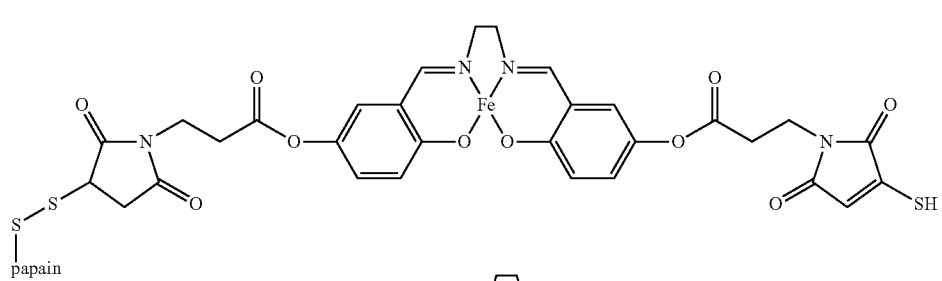

Compound 12

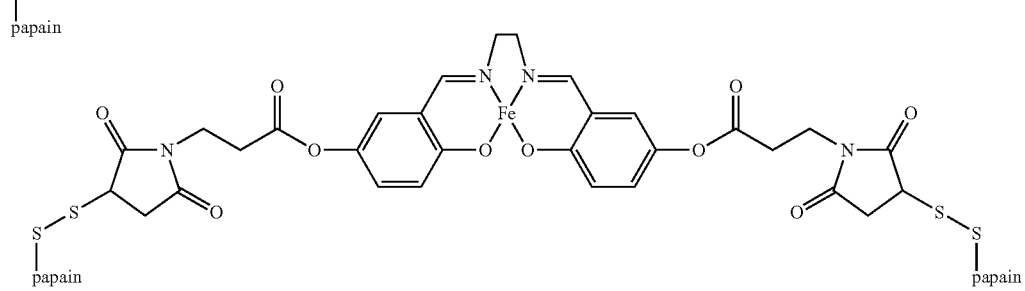

An iron-salen complex including a carboxyl group was produced in accordance with the above-described steps by using 3-hydroxybenzoic acid as a starting material. Then, the iron-salen complex, N'-dicyclohexyl carbodiimide (DCC), and hydroxysuccinimide (HONSu) were made to react to each other, thereby generating an active ester; and when protein (papain-lyophilisate), which was a target substance, was made to react to the active ester, the protein substituted the hydroxysuccinimide and bound to the iron-salen complex via an amide bond. The amide bond was confirmed by infrared spectrophotometer.

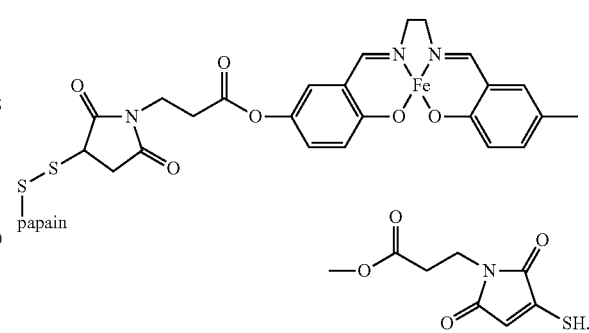

The invention claimed is:

1. An iron-salen complex derivative of formula

2. A method of producing an iron-salen complex derivative of formula

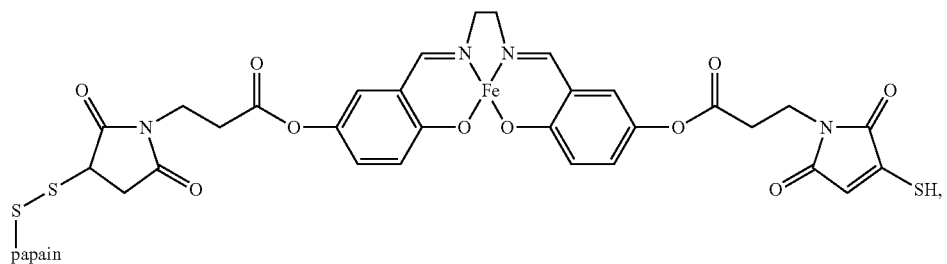
the method comprising binding a functional molecule to an iron salen complex via a bond area, wherein:
the functional molecule is papain;
the iron salen complex is
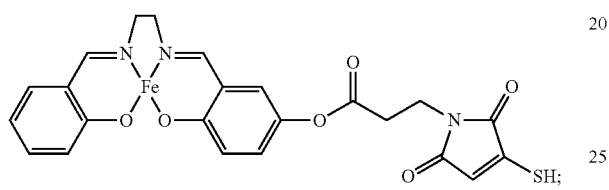
and
the bond area is
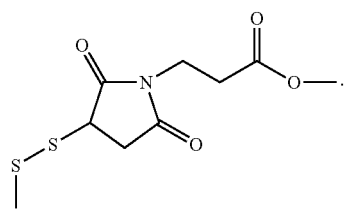 [SMILES: COC(=O)CCN1C(=O)CC(SSC)C1=O]
* * * * *